United States Patent [19]

Dahn

[11] Patent Number: 4,644,574
[45] Date of Patent: Feb. 17, 1987

[54] METHOD AND APPARATUS FOR DETECTING HETEROGENEITIES IN PIPE INSULATION WITH X-RAYS

[76] Inventor: Stig Dahn, S. Skogsrundan 47, S-184 00 Akersberga, Sweden

[21] Appl. No.: 753,486

[22] Filed: Jul. 10, 1985

[30] Foreign Application Priority Data

Aug. 27, 1984 [SE] Sweden .............................. 84042480

[51] Int. Cl.⁴ .............................................. G01B 15/06
[52] U.S. Cl. ........................................... 378/58; 378/59
[58] Field of Search ................ 378/58, 59; 250/358.1, 250/359.1

[56] References Cited

U.S. PATENT DOCUMENTS

| | | | |
|---|---|---|---|
| 2,396,069 | 3/1946 | Zapp | 378/59 |
| 3,080,479 | 3/1963 | Berg et al. | 378/58 |
| 3,108,186 | 10/1963 | Flavell, Jr. | 378/59 |
| 4,542,520 | 9/1985 | Nelson | 378/59 |

Primary Examiner—Janice A. Howell
Attorney, Agent, or Firm—Sughrue, Mion, Zinn, Macpeak and Seas

[57] ABSTRACT

A method and apparatus for detecting with the aid of X-ray radiation, caused to act upon a film or the like (5), heterogeneities in joints between mutually adjacent sections of insulation (4) on pipe assemblies comprising an inner steel pipe (3), insulation (4), and a tubular jacket (2). The novel features of the invention reside in bringing the radiation transmitted from an X-ray radiation source (1) of low-energy type, in at least two mutually sequential exposure stages to contact the steel pipe at at least one point thereon or along at least one tangential line ($T_1$, $T_2$) and to pass through the insulation (4) along the whole of that part of the radius of the jacket (2) which lies between the contact point line and the inner defining surface (8) of the jacket; and in that the axis (6) of the X-ray radiation source (1) lies in a plane which is substantially perpendicular to the longitudinal axis of the steel pipe.

7 Claims, 4 Drawing Figures

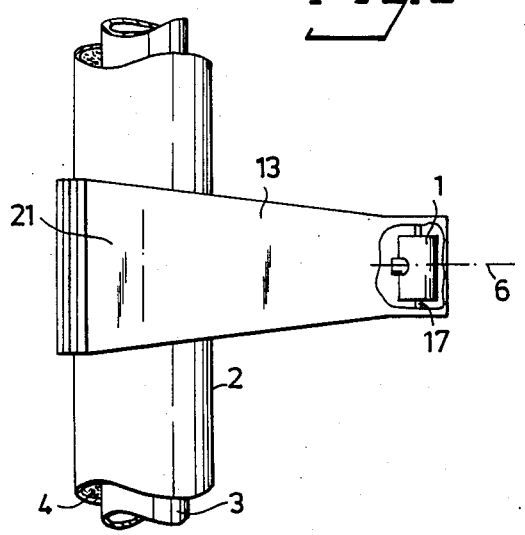

METHOD AND APPARATUS FOR DETECTING HETEROGENEITIES IN PIPE INSULATION WITH X-RAYS

BACKGROUND OF THE INVENTION

The present invention relates to a method of detecting with the aid of X-ray radiation heterogeneities in joints located between sections of insulation on pipe assemblies in communal or district heating systems and in the insulating material itself, using a radiation sensitive material, such as a film, said pipe assemblies being of the kind which incorporate an inner steel pipe, a tubular plastics jacket encasing the steel pipe and spaced radially therefrom, and a foamed plastics insulation which fills the space between the steel pipe and the jacket therearound. The invention also relates to an apparatus for carrying out the method.

In recent years damage caused by corrosion of the steel pipes of district heating systems has become particularly serious. This corrosion is caused by water penetrating cracks and apertures in the tubular jacket, or in adjacent tubular lengths thereof.

These water entry points are created in many instances by heterogeneities in the insulation of the straight pipes, and in the foam mouldings at the joint locations. One normally found heterogeneity comprises bubble formations in the insulating material, which nomally comprises polyurethane foam, unfilled sections, or open gaps at locations where the insulation at the joints connects with the insulation of the straight pipes. When an air-filled space forms in a joint or in the insulation present between mutually joined sections, an abnormally large quantity of heat is transported from the steel pipe conducting hot water, out to the tubular jacket or to the sealing sleeve embracing a joint, via this unfilled space. Because the hot water has a temperature which reaches 120° C., and because the tubular jacket is made of a plastics material, such as polyethylene, whose plastizing temperature often lies beneath 100° C., this heat transportation will cause the jacket material to soften. The soil-stone filling surrounding the jacket is then able to deform the softened part thereof and rapidly cause the jacket to be punctured, whereupon water enters the insulation and initiates corrosion of the steel pipe. Such heat transportation is particularly critical in those instances where shrink sleeves are used at the joints, since the tensioning force exerted by the sleeves, and therewith their sealing ability, ceases in the presence of high temperatures.

It is therefore of the greatest importance that the foamed plastics insulation at the joint locations is free from air bubbles or unfilled voids capable of creating abnormal heat transfers.

The opportunities of checking the quality of the foamed plastics injected into the joint between two pipe lengths on the working site are very slight and in practice are limited to visual inspections. The possibilities of making such quality checks in the case of the filling in the space between the steel pipe and the tubular jacket, which is normally concentric with the steel pipe, are also very limited. The only possibility of making quality checks at present involves the destructive removal of samples. In addition hereto, it is possible by means of the X-ray method to establish the moisture content of the insulation within certain limits, for example the ends of straight pipes or, for example, at excavated joint locations where water leakage is suspected.

Attempts have been made to examine such insulation with the aid of conventional X-ray techniques. The results, however, have been negative, due to the fact that the steel pipe absorbs so much of the radiation that the radiation is unable to reach parts of the insulation lying therebeneath, and that if an attempt is made to reach the underlying parts of the insulation, by increasing the level of radiation energy transmitted thereto, insufficient contrast is obtained, thereby making it impossible to discover voids and like unfilled parts.

SUMMARY OF THE INVENTION

Consequently, an object of the present invention is to provide a method and apparatus with which heterogeneities can be detected in the insulation of straight pipes and at the joints between mutually adjacent pipes, with the aid of simple, lightweight apparatus capable of being used at the working site, and with the aid of X-ray radiation transmitted tangentially in relation to a steel pipe.

BRIEF DESCRIPTION OF THE DRAWINGS

The invention will now be described in detail with reference to the accompanying drawings, in which FIG. 1 illustrates the principle of the invention;

FIG. 2 is a simplified illustration of an exemplifying embodiment of apparatus according to the invention, and shows the apparatus in position on a pipe assembly incorporated in a district heating system;

FIG. 3 illustrates the apparatus of FIG. 2 from above; and

FIG. 4 is a sectional view taken on the line IV—IV in FIG. 2.

DETAILED DESCRIPTION OF THE PREFERRED EMBODIMENT

FIG. 1 illustrates an X-ray source 1 located at a determined, or at least substantially determined distance A from the outer peripheral surface of a tubular plastics jacket 2 concentrically encircling a hot-water carrying steel pipe 3. The annular space between the pipe 3 and the jacket 2 is filled with a heat-insulating foamed plastics 4. The X-ray source 1 transmits towards the pipe of the district heating system a conical beam of rays, of cone angle $\alpha$, which contacts an X-ray sensitive medium 5, for example an X-ray film, located on the side of the pipe remote from the source 1, preferably perpendicular to the centre axis 6, of the radiation source 1, i.e. the axis of radiation. The radiation axis 6 lies in a plane at right angles to the centre axis 7 of the steel pipe 3.

According to the invention the X-ray source 1 is of low-energy kind, i.e. it transmits relatively soft radiation. The working voltage suitably lies within the range 20–40 kV. When penetrating the foamed plastics insulation 4 with radiation of this nature, an extremely good contrasting effect is obtained, and any empty voids or any air bubbles present can be readily discerned subsequent to developing the films 5, or preferably a paper sensitive to X-rays which can be quickly developed and which produces a positive image or picture.

The steel pipe 3 will absorb all of the X-ray radiation, and the film or paper will therefore only be exposed to that part of the radiation which lies within the angles $\alpha_1$ and $\alpha_2$ respectively. These two sections of the X-ray beam penetrate the insulation in segmental areas between a line $T_1$, tangential to the circumference of the pipe 3, and the inner surface 8 of the tubular jacket 2. The two parts of the insulation through which the beam passes are hatched and are referenced 9 and 10 respectively. In order to check those areas through which the beam does not pass, the radiation source is rotated around the culvert pipe in the direction of the arrow B, to one or more further exposure stations, so as to check the insulating material around the full circumference of the pipe. The film 5 is changed between exposures. In order for the exposures to be taken correctly and in a reproduceable manner, and in order to enable the possible presence of discontinuities to be established for possible local repair work, the distance A must be maintained in all of the exposure stations, which implies in practice that the X-ray source must be fixed in relation to the pipe. Similarly, the cassette or cassettes containing the medium 5 sensitive to X-ray radiations must also be held aligned in specific positions relative to the radiation axis 6 of the source 1 and held at a constant distance from the source 1, so that the pictures obtained can be reliably interpreted and the necessary contrast effect obtained. When there is doubt as to the position of a discontinuity, i.e. when the discontinuities lie in a region located closer to the radiation source or to the film, a stereo-technique can be readily applied, by moving the radiation source in the direction B (rotation relative to the culvert pipe). The locations of discontinuities can be determined accurately, with the aid, for example, of a grid fixed to the tubular jacket and included in the photographs taken, and knowledge of the extent to which the source is moved in the B-direction.

FIG. 1 illustrates an X-ray beam source which fully embraces the pipe of the district heating system and where the beam generated by said source passes tangentially to the steel pipe 3 along two mutually opposed lines $T_1$ and $T_2$. It will be understood, however, that there can be used instead an X-ray beam which contacts the pipe 3 tanentially on solely one side thereof, for example a beam having the cone angle $\alpha$ in FIG. 1.

FIGS. 2–4 illustrate apparatus according to the invention, comprising a casing which surrounds the beam generated by the X-ray beam source 1. The casing is divided into two parts, and is made, for example, of sheet aluminium, the inner surfaces of which are lined with lead foil or the like, to attenuate stray radiation occuring when using low-energy apparatus. The casing consists of a first half 11 with side plates 12 which connect with a plate 13, and a second half 14 with side plates 15 connecting with a plate 16. The two casing halves, which can be swung in towards each other to form a funnel-shaped and adjustable shield, are connected at their respective ends by means of a hinge 17 at the focus of the radiation source 1, and present abutments 19 and 20 on the open end 18 of said casing halves remote from the beam source, these abutments being intended to lie against the peripheral surface of a tubular jacket 2 and therewith determine the distance between the X-ray beam source 1 and the pipe assembly of the district heating system. Located at the end parts of the casing are two protective plates 21 and 22 which grip around the tubular jacket of the pipe assembly and which carry on their respective end surfaces 23, 24 two lead plates 25 and 26. A film cassette 5 is placed in each of the respective spaces between 23, 25 and 24, 26. The cassette at 25 co-acts with the left-hand part of the beam in FIG. 1, while the cassette at 26 co-acts with the right-hand part of the beam in FIG. 1.

The apparatus illustrated in FIGS. 2–4, which can be modified in many ways within the scope of the inventive concept, can be readily handled and operated and ensures that the radiation source 1 will always lie at a constant distance from the pipe assembly during the mutually following exposure sequencies during which X-rays pass through the pipe assembly, and that the X-ray sensitive medium 5 will also always lie at a constant distance from the radiation source. The casing 11, 14 forms a reliable shield against stray radiation. Picture-quality indicators can be placed in the casing, at the positions indicated by references 21 and 22, and included in the photographs taken. The picture-quality indicators may comprise, for example, blocks of foamed plastics incorporating different reference faults, for example drilled holes of different diameters.

The illustrated two-piece casing, comprising two halves mutually hinged so that they can be swung towards and away from one another, may be replaced with a rigid casing which is intended to be placed over that part of the pipe assembly to the examined.

I claim:

1. A method of detecting heterogeneities in foamed plastic insulation material (4) surrounding a tubular steel pipe (3) or in joints between adjacent and abutting sections of such insulation material, said insulation material in turn being surrounded by and encased within a tubular plastic jacket (2) radially spaced from the pipe, comprising the steps of:
   (a) disposing a source (1) of low energy X-ray radiation at a position on one side of the jacket and radially outwardly spaced therefrom such that an axis (6) of a conical beam of radiation emitted by said source lies in a plane substantially perpendicular to a longitudinal axis (7) of the pipe,
   (b) disposing a sheet of X-ray sensitive material (5) on another, opposite side of the jacket and substantially perpendicular to said beam axis such that radiation from the source passes through at least one chordal section (9, 10) of insulation and jacket material tangent to the pipe to expose the sheet with an image thereof, with radiation from the source impinging on the pipe being blocked and absorbed thereby, and
   (c) disposing both the source and a fresh sheet of X-ray sensitive material in respective rotationally displaced positions on opposite sides of the pipe to expose the fresh sheet with an image of at least one different chordal section of insulation and jacket material, such that successive, rotationally advanced images are obtained to enable the detection of heterogeneities in the full circumference of the insulation material.

2. A method according to claim 1, wherein two chordal section exposures on substantially opposite sides of the pipe are obtained in each of steps (b) and (c).

3. A method according to claims 1 or 2, wherein the radiation source is maintained at a constant radial distance from the longitudinal axis of the pipe in steps (b) and (c).

4. An apparatus for detecting heterogeneities in foamed plastic insulation material (4) surrounding a tubular steel pipe (3) or in joints between adjacent and abutting sections of such insulation material, said insulation material in turn being surrounded by and encased within a tubular plastic jacket (2) radially spaced from the pipe, comprising:
   (a) an elongate radiation absorbing casing (11, 14), (b) a source (1) of low energy X-ray radiation mounted within a first, outwardly extending end of the casing such that an axis (6) of a conical beam of radiation emitted by the source propagates down the length of the casing and is substantially enclosed thereby, (c) abutment means (19, 20) defined by an intermediate portion of the casing for engaging an outer surface of the jacket to position the source at a predetermined distance therefrom with the beam axis lying in a plane substantially perpendicular to a longitudinal axis (7) of the pipe, (d) an opening (18) defined by the casing between the abutment means and a second, opposite end of the casing for embracing the jacket in a jaw-like manner, (e) holder means (25, 26) provided on the second end of the casing for mounting at least one sheet of radiation sensitive material (5) on an opposite side of the jacket from the abutment means and substantially perpendicular to the beam of radiation such that radiation from the source passes through at least one chordal section (9, 10) of insulation and jacket material tangent to the pipe to expose the sheet with an image thereof, with radiation from the source impinging on the pipe being blocked and absorbed thereby, and (f) a pair of radiation shields (21, 22) provided on the casing between the abutment means and the inner end of the casing and flanking the opening to overlie opposite sides of the jacket, (g) said apparatus being displaced to successive circumferential positions about the jacket to obtain a sequence of rotationally advanced images so as to enable the detection of heterogeneities in the full circumference of the insulation material.

5. Apparatus according to claim 4, wherein the X-ray radiation from the source produces two chordal section exposures on substantially opposite sides of the steel pipe.

6. Apparatus according to claims 4 or 5, wherein the casing comprises two shell members (11, 14) which can be swung towards and away from one another.

7. Apparatus according to claim 6, wherein the two shell members are pivotably hinged at one end about an axis (17) which passes through a focus of the X-ray radiation source.

* * * * *